United States Patent
Nesvadba et al.

(10) Patent No.: US 8,940,806 B2
(45) Date of Patent: Jan. 27, 2015

(54) POLYMERIZABLE COMPOSITIONS

(75) Inventors: Peter Nesvadba, Marly (CH); Lucienne Bugnon Folger, Pfeffingen (CH); Jean-Luc Birbaum, Binningen (CH); Marc Faller, Hegenheim (FR); Antoine Carroy, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 7 days.

(21) Appl. No.: 13/258,951

(22) PCT Filed: Mar. 26, 2010

(86) PCT No.: PCT/EP2010/053969
§ 371 (c)(1),
(2), (4) Date: Oct. 25, 2011

(87) PCT Pub. No.: WO2010/112410
PCT Pub. Date: Oct. 7, 2010

(65) Prior Publication Data
US 2012/0041093 A1    Feb. 16, 2012

(30) Foreign Application Priority Data

Mar. 30, 2009 (EP) .................................... 09156625
Apr. 27, 2009 (EP) .................................... 09158837

(51) Int. Cl.
| | | |
|---|---|---|
| C08F 2/10 | (2006.01) | |
| C08F 2/50 | (2006.01) | |
| B29C 71/04 | (2006.01) | |
| C08F 2/46 | (2006.01) | |
| C08G 61/04 | (2006.01) | |
| C08F 4/04 | (2006.01) | |
| C07D 211/98 | (2006.01) | |
| C09D 175/14 | (2006.01) | |

(52) U.S. Cl.
CPC ............. C08F 4/04 (2013.01); C07D 211/98 (2013.01); C08F 2/46 (2013.01); C09D 175/14 (2013.01)
USPC ............. 522/63; 522/6; 522/71; 522/1; 520/1

(58) Field of Classification Search
CPC .... C08F 2/50; C08F 299/028; C08F 299/026; C07D 249/00; G03C 1/30; G03C 1/305; C09K 19/3828; C08K 5/3492
USPC ................... 522/63, 6, 71, 1; 520/1
See application file for complete search history.

(56) References Cited

U.S. PATENT DOCUMENTS

| | | | |
|---|---|---|---|
| 3,844,916 A | 10/1974 | Gaske | |
| 4,619,956 A | 10/1986 | Susi | |
| 5,198,498 A | 3/1993 | Valet et al. | |
| 5,298,067 A | 3/1994 | Valet et al. | |
| 5,322,868 A | 6/1994 | Valet et al. | |
| 5,369,140 A | 11/1994 | Valet et al. | |
| 5,482,649 A | 1/1996 | Meixner et al. | |
| 5,734,002 A | 3/1998 | Reich et al. | |

FOREIGN PATENT DOCUMENTS

| | | | |
|---|---|---|---|
| EP | 0 280 222 | | 8/1988 |
| EP | 0 434 608 | | 6/1991 |
| EP | 0 704 437 | | 4/1996 |
| GB | 2 297 091 | | 7/1996 |
| WO | 94 18278 | | 8/1994 |
| WO | 96 28431 | | 9/1996 |
| WO | 01 90113 | | 11/2001 |
| WO | 2004 081100 | | 9/2004 |
| WO | 2005 030852 | | 4/2005 |
| WO | 2006 051047 | | 5/2006 |
| WO | WO 2006/046736 | * | 5/2006 |
| WO | 2010/079102 | | 7/2010 |

OTHER PUBLICATIONS

Lodovico Lunazzi, Conformational Studies by Dynamic Nuclear Magnetic Resonance, Journal of the Chemical Society, Perkin Transactions 2: Physical Organic Chemistry, 1978, Issue 7, pp. 686-691.*
D. B. Kimball, et al.; J/A/C/S/ Articles Published on Web Oct. 19, 2002; Deciphering the Mechanistic Dichotomy in the Cyclization of 1-(2-Ethynylphenyl)-.3,3-dialkyltriazenes: Competition between Pericyclic and Pseudocoarctate Pathways; J.AM. Chem. Soc. 2002, 124, pp. 13463-13473.
International Search Report Issued Jun. 23, 2010 in PCT/EP10/053969 Filed Mar. 26, 2010.
First Office Action issued Jun. 26, 2013 in corresponding Chinese Application for Invention No. 2010800148136 with English Translation (3pp.).
English language translation of Text of the Second Office Action Cited in Chinese Patent Application for Invention No. 2010800148136 in receipt of observations submitted Nov. 11, 2013.
Communication pursuant to Article 94(3) EPC in Application No. 10 710 350.0-1304 Ref C000023983 Dated Feb. 28, 2013.

* cited by examiner

*Primary Examiner* — Ling Choi
*Assistant Examiner* — Jessica E Whiteley
(74) *Attorney, Agent, or Firm* — Oblon, Spivak, McClelland, Maier & Neustadt, L.L.P.

(57) ABSTRACT

The invention relates to the use of triazenes of formula (I) wherein Q is a direct bond or a bivalent radical —$(CR_8R_9)$—, $Z_1$ is —O—, —$NR_{10}$—, —$CH_2$—, —$(CR_{11}R_{12})$— or —C(=O)— and $R_1$ to $R_{12}$ are optionally substituted hydrocarbon residues, as precursors for radicals useful in reactions triggered by free radicals, such as polymerization of unsaturated monomers and degradation of polyolefins. Most of the triazenes of formula (I) are novel and claimed, too, as well as the preparation of triazenes of formula (I) and polymerizable compositions comprising them.

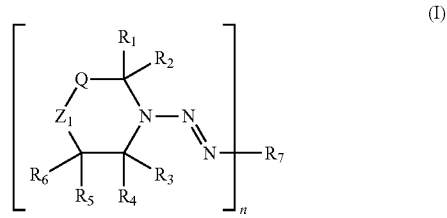

(I)

20 Claims, No Drawings

POLYMERIZABLE COMPOSITIONS

The invention relates to the use of triazene compounds as source of radicals (in particular as polymerization initiators), to polymerizable compositions comprising these triazenes and to new triazene compounds.

Free-radical polymerization belongs to the most important polymerization methods. It is used for preparing many commercially important polymers such as polystyrene, PVC, polyacrylates, polymethacrylates, PAN and other polymers. For technical details, reference may be made to the still relevant standard work G. Odian, Principles of Polymerization, McGraw-Hill New York 1991.

Free-radical polymerizations are started using initiators. Examples of initiators which have become established in polymer technology are azo compounds, dialkyl peroxides, diacyl peroxides, hydroperoxides, thermolabile C—C-dimers, redox systems and photoinitiators. Reference is made to the "Handbook of Free Radical Initiators", (E. T. Denisov, T. G. Denisova, T. S. Pokidova, J. Wiley & Sons, Inc. Hoboken, N.J., 2003).

Despite their widespread use, the known polymerization initiators have various disadvantages. Thus, for example, peroxides are extremely readily ignitable and sustain fire and present thus potential explosion hazards, so that their manufacture, storage, transport and use has to involve costly safety precautions. Some initiators further generate toxic products, as e.g. AIBN.

There is therefore a general need for new initiators for free-radical polymerization processes which have a satisfactory safety profile.

WO2001/90 113A1, WO2004/081 100A1 and WO2006/051 047A1 more recently disclosed sterically hindered N-acyloxyamines and N-substituted imides as new classes of polymerization initiators.

EP 09 150 183.3 (8.1.2009), which relates to isoureas as polymerization initiators, is a European patent application according to Art. 54(3) EPC and Rule 64.3 PCT.

We have now developed specific triazene compounds which behave as efficient initiators of free radical polymerization or of other processes which are triggered off by free radicals, for example controlled the degradation of polyolefins. Though there is no duty for inventors to give any theoretical explanations, we believe that the mechanism of this action is due to the homolytical cleavage of the inventive triazenes which leads to polymerization effective free radicals according to the following equation:

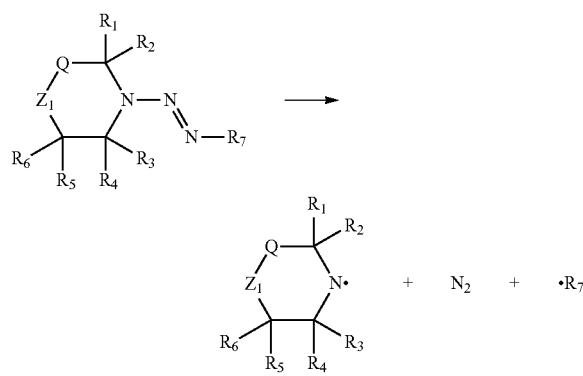

The stimulus triggering the radical generation can be heat, infrared or near infrared radiation or visible light of a suitable wavelength. Photochemical and thermochemical decomposition of triazenes each leading to free radicals have been reported by O. Nuyken et al. (Makromol. Chem. 194, 3385 [1993]) and K. Albert et al. (Bull. Chem. Soc. Jap. 49, 2537 [1976]), respectively.

Additionally, the stimulus triggering the radical generation can be a redox reaction induced by suitable redox-active species such as e.g. ascorbic acid, glucose, hydroquinone or iron (II) sulphate. Such redox initiated decompositions of triazenes are described by V. Ya. Andakuskin et al. (Zh. Obsh. Khim. 26, 3789 [1956]).

The inventive polymerization effective triazenes are of formula

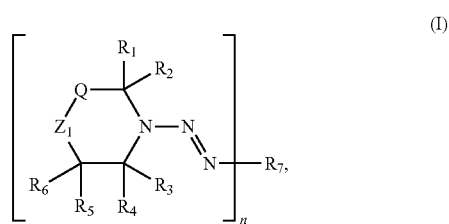

wherein

Q is a direct bond or a bivalent radical —$(CR_8R_9)$—;

$Z_1$ is —O—, —$NR_{10}$—, —$CH_2$—, —$(CR_{11}R_{12})$— or —C(=O)—, preferably —$(CR_{11}R_{12})$—;

$R_1$ and $R_2$ are each independently from the other $C_1$-$C_6A_{LK}$yl, or $R_1$ and $R_2$ are together $C_4$-$C_7A_{LK}$ylene, thus forming a preferably 5-, 6-, 7- or 8-membered cyclic group with the C-atom to which they are attached;

$R_3$ and $R_4$ are each independently from the other $C_1$-$C_6A_{LK}$yl, or $R_3$ and $R_4$ are together $C_4$-$C_7A_{LK}$ylene, thus forming a preferably 5-, 6-, 7- or 8-membered cyclic group with the C-atom to which they are attached;

$R_5$ and $R_6$ are each independently from the other H, $C_1$-$C_6A_{LK}$yl, $C_6$-$C_{10}$aryl or $C_7$-$C_{12}$ar$A_{LK}$yl, or $R_5$ and $R_6$ are together oxygen, thus forming a carbonyl group together with the C-atom to which they are attached;

$R_7$ is $C_6$-$C_{24}$aryl, $C_7$-$C_{24}$ar$A_{LK}$yl, $C_1$-$C_{24}$heteroaryl or $C_2$-$C_{24}$heteroar$A_{LK}$yl;

$R_8$ and $R_9$ are each independently from the other H or $C_1$-$C_6A_{LK}$yl;

$R_{10}$ is hydrogen, $C_1$-$C_6A_{LK}$yl, $C_6$-$C_{10}$aryl or —O—C(=O)—$R_{13}$;

$R_{11}$ is hydrogen or $C_1$-$C_6A_{LK}$yl;

$R_{12}$ is $R_{14}$, C(=O)—$R_{14}$, CN, OH, $OR_{14}$, $NH_2$, $NHR_{14}$, $NR_{14}R_{15}$, O—C(=O)—$R_{16}$, NH—C(=O)—$R_{16}$ or $NR_{14}$—C(=O)—$R_{16}$, preferably OH, $OR_{14}$, $NH_2$, $NHR_{14}$, $NR_{14}R_{15}$, O—C(=O)—$R_{16}$, NH—C(=O)—$R_{16}$ or $NR_{14}$—C(=O)—$R_{16}$;

or $R_{11}$ and $R_{12}$ are together $C_2$-$C_{20}A_{LK}$ylene which is uninterrupted or once or twice interrupted by —O— and/or —$NR_{17}$—, thus forming a preferably 5- or 6-membered ring with the C-atom to which they are attached, which $C_2$-$C_{20}A_{LK}$ylene can optionally be annelated with benzo or naphtho, and which $C_2$-$C_{20}A_{LK}$ylene is further unsubstituted or substituted by 1 or 2, identical or different groups —OH or —O—C(=O)—$R_{13}$;

$R_{13}$ is H, $R_{18}$, $OR_{18}$, $NR_{18}R_{19}$, $COOR_{20}$, $R_{21}$—$COOR_{20}$ or $R_{22}$(—$COOR_{20}$)—$COOR_{23}$;

$R_{14}$ and $R_{15}$ are each independently from the other $C_1$-$C_6A_{LK}$yl, $C_7$-$C_{12}$ar$A_{LK}$yl or $C_8$-$C_{10}$aryl;

or $R_{14}$ and $R_{15}$ are together $C_2$-$C_6A_{LK}$ylene which is uninterrupted or once or twice interrupted by —O— and/or —$NR_{17}$—, thus forming a preferably 5- or 6-membered ring with the N-atom to which they are attached;

$R_{16}$ is H, $R_{18}$, $OR_{18}$, $NR_{18}R_{19}$, $COOR_{20}$, $R_{21}$—$COOR_{20}$ or $R_{22}$(—$COOR_{20}$)—$COOR_{23}$;

$R_{17}$ is H or $C_1$-$C_6A_{LK}$yl;

$R_{18}$ and $R_{19}$ are each independently from the other $C_1$-$C_{36}A_{LK}$yl, $C_2$-$C_{54}A_{LK}$enyl, $C_2$-$C_{24}A_{LK}$inyl, $C_6$-$C_{10}$aryl, $C_7$-$C_{46}$ar$A_{LK}$yl or $C_2$-$C_{36}A_{LK}$enylene-$C_6$-$C_{10}$aryl;

or $R_{18}$ and $R_{19}$ are together $C_2$-$C_{36}A_{LK}$ylene or $C_2$-$C_{54}A_{LK}$enylene which is uninterrupted or once or twice interrupted by —O— and/or —$NR_{17}$—, thus forming a preferably 5- or 6-membered ring with the N-atom to which they are attached;

$R_{21}$ is $C_1$-$C_{12}A_{LK}$ylene, $C_2$-$C_{12}A_{LK}$enylene, $C_2$-$C_{12}A_{LK}$inylene, $C_6$-$C_{10}$arylene, $C_7$-$C_{18}$ar$A_{LK}$ylene or $C_2$-$C_{18}A_{LK}$enylene-$C_6$-$C_{10}$arylene;

$R_{22}$ is $C_1$-$C_{12}A_{LK}$antriyl, $C_2$-$C_{12}A_{LK}$entriyl, $C_3$-$C_{12}A_{LK}$intriyl, benzotriyl, naphthotriyl, $C_7$-$C_{18}$benzo$A_{LK}$antriyl, $C_{11}$-$C_{22}$naphtho$A_{LK}$antriyl, $C_2$-$C_{12}A_{LK}$antriyl-$C_6$-$C_{10}$arylene, $C_2$-$C_{12}A_{LK}$enylene-benzotriyl, $C_2$-$C_{12}A_{LK}$enylene-naphthotriyl or $C_2$-$C_{12}A_{LK}$entriyl-$C_6$-$C_{10}$arylene;

each $R_{20}$ or $R_{23}$ stands independently from any other $R_1$, $R_2$, $R_3$, $R_4$, $R_5$, $R_6$, $R_7$, $R_{11}$, $R_{18}$, $R_{19}$, $R_{20}$ or $R_{23}$ for H, $R_{18}$, $OR_{18}$, $NR_{18}R_{19}$, $COOR_{20}$, $R_{21}$—$COOR_{20}$, $R_{22}$(—$COOR_{20}$)—$COOR_{23}$ or $$\left[ \begin{array}{c} \text{structure with } R_1, R_2, Q, Z_1, R_6, R_5, R_4, R_3, N-N, N-R_7 \end{array} \right];$$

$A_{LK}$ stands for a linear or once or several times branched and/or mono- or polycyclic hydrocarbon residue including spiro residues, in which hydrocarbon residue one or more —$CH_2$— groups may be replaced by —S— or —NH—, one or more

—CH⟨ groups may be replaced by

—N⟨ and/or one or more non-adjacent —$CH_2$— groups may be replaced by —O—;

each hydrocarbon residue $A_{LK}$ in $R_1$, $R_2$, $R_3$, $R_4$, $R_5$, $R_6$, $R_7$, $R_8$, $R_9$, $R_{10}$, $R_{11}$, $R_{14}$, $R_{15}$, $R_{17}$, $R_{18}$, $R_{19}$, $R_{21}$ and $R_{22}$ is independently from all others unsubstituted or substituted by one or more identical or different substituents selected from the group consisting of Br, Cl, F, I, $NO_2$, $OR_{24}$, $SR_{24}$, SCN, CN, $N(R_{24})R_{25}$, $N(R_{24})$—C(=O)—$R_{25}$, $N(R_{24})$—$COOR_{25}$, $N(COR_{24})COR_{25}$, $COOR_{24}$, $$COO^- \left[ \frac{1}{m} M^{m+} \right],$$

$COR_{24}$, O—C(=O)$R_{24}$, C(=O)$NR_{24}R_{25}$, O—C(=O)$NR_{24}R_{25}$, O—C(=O)$NR_{24}$, $R_{25}$, $$SO_3H, SO_3^- \left[ \frac{1}{m} M^{m+} \right],$$

$SO_2NR_{24}R_{25}$, S(=O)$R_{24}$, $SO_2R_{24}$ and P(=O)(O$R_{24}$)O$R_{25}$;

$R_{24}$ and $R_{25}$ are each independently from any other H, $C_1$-$C_{18}$alkyl, $C_7$-$C_{18}$aralkyl, $C_6$-$C_{24}$aryl or $C_1$-$C_{24}$heteroaryl;

or $R_{24}$ and $R_{25}$ are each independently from any other H, $C_1$-$C_{18}$alkyl, $C_7$-$C_{18}$aralkyl, $C_6$-$C_{24}$aryl or $C_1$-$C_{24}$heteroaryl, and $R_{24}$ and $R_{25}$ are additionally bound together through a direct bond or bridged over a O, S, NH, N—$C_1$-$C_{18}$alkyl, N—$C_7$-$C_{18}$aralkyl, N—$C_6$-$C_{24}$aryl or N—$C_1$-$C_{24}$heteroaryl bridge;

$M^{m+}$ is an organic or inorganic cation;

m is 1, 2, 3 or 4; and n is 1, 2, 3 or 4, preferably 1 or 2.

The residue '$A_{LK}$' is instantly used instead of 'alk' or 'cycloalk' in combination with standard IUPAC terminology except for the optional oxa-, thia- or aza-substitution being omitted, depending on its number of free valences and eventual presence of double or triple bonds, '$A_{LK}$ene' standing for residues comprising one or more double bonds as well as optionally single bonds however excluding aromatic residues and '$A_{LK}$ine' standing for residues comprising one or more triple bonds as well as optionally single and/or double bonds, the maximal number of double and triple bonds in said residue '$A_{LK}$ene' or '$A_{LK}$ine' being totally no more than one half of the number of C atoms in said residue '$A_{LK}$ene' or '$A_{LK}$ine'.

$C_6$-$C_{24}$Aryl, $C_7$-$C_{24}$ar$A_{LK}$yl, $C_1$-$C_{24}$heteroaryl and $C_2$-$C_{24}$heteroar$A_{LK}$yl can be mono- or polycyclic, condensed or conjugated, or two or more aromatic or heteroaromatic groups may be bridged with an alkylene group. $C_6$-$C_{24}$Aryl, $C_7$-$C_{24}$ar$A_{LK}$yl, $C_1$-$C_{24}$heteroaryl or $C_2$-$C_{24}$heteroar$A_{LK}$yl are for example phenyl, benzyl, naphthyl, indyl, indenyl, fluorenyl, acenaphthyl, biphenylyl, anthracyl, o-, m- or p-terphenyl.

$NR_{24}R_{25}$ is for example dimethylamino, diethylamino or dibutylamino, or, when $R_{24}$ and $R_{25}$ are additionally bound together through a direct bond or over a bridge, further morpholino, pyrrolidino, piperidino, 4-methyl-1-piperazinyl or carbazol-9-yl.

The maximal number of substituents in each hydrocarbon residue $A_{LK}$ is equal to the number of hydrogens which can be substituted. For example, it is possible part or all hydrogens to be substituted, such as in trifluoromethyl, 2,2,2-trifluoroethyl or perfluoropentyl. There can, however, also be different substituents on the same hydrocarbon residue $A_{LK}$.

In bivalent and trivalent groups, the valences can be in any position. For example, phenylene is o-, m-, or p-$C_6H_4$, and in alkylene or alkanetriyl the valences may be geminal, terminal or in any other intermediate position.

$M^{m+}$ is for example a $Na^+$, $K^+$, $Ca^{2+}$, $Mg^{2+}$, $Al^{3+}$, $AlCl^{2+}$, $AlOH^{2+}$, $Zr^{4+}$, $ZrO^{2+}$, $NH_4^+$, $N^+(C_1$-$C_{24}$alkyl$)_4$ or any other inorganic, organometallic or organic cation. The nature of $M^{m+}$ is not essential for the performance of the instant compounds.

The inventive compounds of formula (I) are prepared, for example, in close analogy to known methods, such as:

Coupling amines with diazonium salts for example according to the conditions disclosed by J. Benson ("The high nitrogen compounds", J. Wiley and Sons [1984]), L. Lunazzi et al. (J. Chem. Soc. Perkin II, 686-691 [1978]) or Ch. S. Rondestvedt and S. J. Davis (J. Org. Chem. 200-203 [1957]):

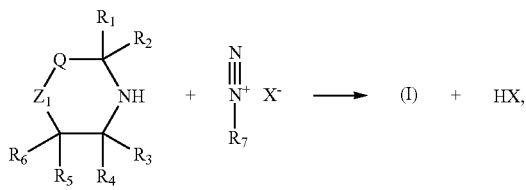

the diazonium salts being most conveniently prepared through diazotation of aromatic or heteroaromatic amines as described by, e.g., H. Zollinger ("Diazochemistry I", VCH [1994]).

Examples of suitable amines are aniline; o-, m-, p-chloro-aniline; o-, m-, p-nitro-aniline; o-, m-, p-carboxy-aniline; o-,m-,p-methoxycarbonyl-aniline; p-sulfoaniline; p-aminosulfonyl-aniline; 2,5-dichloro-aniline; 2-methyl-5-chloro-aniline; 2-nitro-4-chloro-aniline; 2-nitro-4-methyl-aniline; 2-nitro-4-methoxy-aniline; 2-methoxy-4-nitro-aniline; 2-trifluoromethy-4-chloro-aniline; 2,5-bis(methoxyacarbonyl)-aniline; 2,4,5-trichloro-aniline; 4-carbamoyl-aniline; 2-methyl-5-carbamoyl-aniline; 2-chloro-5-methylaminocarbonyl-aniline; 2-methoxy-5-phenylaminocarbonyl-aniline; 2-methoxycarbonyl-5-(2,5-dichlorophenyl-amino)-carbonyl-aniline; 2,5-dimethoxy-5-methylaminosulfonyl-aniline; 3,3'-dichloro-benzidine; o-tolidine; o-dianisidine; 2,2',5,5'-tetrachloro-benzidine; 2-sulfo-4-methyl-aniline; 2-sulfo-4-methyl-5-chloro-aniline; 2-sulfo-4-chloro-5-carboxy-aniline; 2-sulfo-4-chloro-5-methyl-aniline; 1-sulfo-2-amino-naphthalene; 2-aminothiazole; 2-amino-5-bromothiadiazole; 2-amino-5-ethyl-1,3,4-thiadiazole; 2-amino-5-methyl-1,3,4-thiadiazole; 2-amino-5-t-butyl-1,3,4-thiadiazole; 2-amino-5-ethylthio-1,3,4-thiadiazole; 2-amino-4,5-dicyano-1H-imidazole; 5-amino-1,3-diphenyl-pyrazole; 5-amino-3-phenyl-1,2,4-thiadiazole and 2-amino-benzothiazole.

Condensation of hydrazines with nitroso-aromates or nitroso-heteroaromates according to the general scheme disclosed, e.g., by R. K. Saksena and M. A. Khan (Indian J. Chem. 443-444 [1989]):

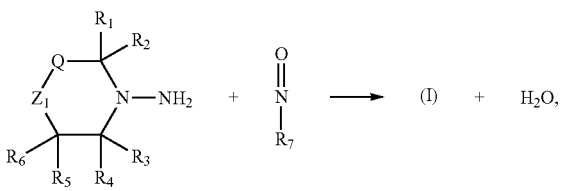

the hydrazines being most conveniently prepared as described, e.g., by W. D. Hinsberg, P. G. Schultz and P. B. Dervan (J. Am. Chem. Soc. 766-773 [1982]), and reacted with well known nitroso-aromates or nitroso-heteroaromates.

Condensation of N-nitrosoamines with aminoaromates or amino-heteroaromates according to the general scheme disclosed, e.g., by L. M. Mironovich, V. K. Promonenkov and S. E. Bogushevich (Khimiya Geterotsiklicheskikh Soedinenii 6, 833-835 [1987]):

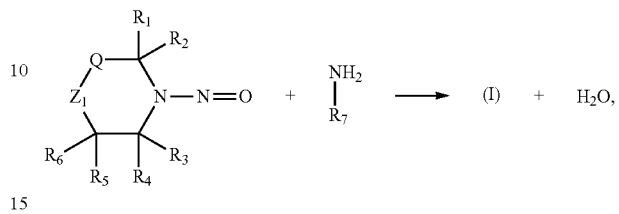

the N-nitrosoamines being most conveniently prepared in analogy to the procedure described, e.g., by W. D. Hinsberg, P. G. Schultz and P. B. Dervan (J. Am. Chem. Soc. 766-773 [1982]).

Condensation of N-alkoxydiazenium salts with aminoaromates or amino-heteroaromates according to the following general scheme:

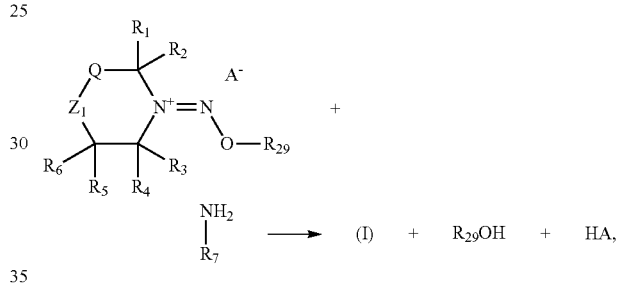

wherein $R_{29}$ is $C_1$-$C_{36}A_{LK}yl$, $C_2$-$C_{54}A_{LK}enyl$, $C_2$-$C_{24}A_{LK}inyl$, $C_6$-$C_{10}aryl$, $C_7$-$C_{46}arA_{LK}yl$ or $C_2$-$C_{36}A_{LK}enylene$-$C_6$-$C_{10}aryl$, $A^-$ is the anion of an inorganic, organometallic or organic acid, and the N-alkoxydiazenium salts being most conveniently prepared and reacted with the amines in analogy to the procedure described, e.g., by G. V. Shustov, N. B. Tavakalyan, L. L. Shustova, I. I. Chervin and R. G. Kostyanovskii (Izvestiya Akademii Nauk SSSR, Seriya Khimicheskaya 5, 1058-1063 [1980])).

The compounds of formula (I) are used as polymerization initiators, polymerization auxiliaries or molecular weight modifiers in polymerizable compositions comprising at least one ethylenically unsaturated, polymerizable monomer or oligomer, preferably in polymerizable compositions used for preparing coatings.

The compounds of formula (I) are further used as flame retardants, for example as disclosed in WO 05/030852, the contents of which are entirely incorporated herein by reference.

The invention therefore further provides a composition comprising (a) an ethylenically unsaturated, polymerizable monomer or oligomer and (b) an effective, thermally or actinically radicals generating amount of a compound of formula (I).

The component (b) is most adequately used in the composition in a molar amount such that from 0.01 to 30, preferably from 0.05 to 10, particularly preferably from 0.1 to 1.0 triazene functional groups N—N=N—$R_7$ are present per 100 ethylenically unsaturated functional groups C=C of the polymerizable monomer or oligomer (a).

It is sufficient for the instant polymerization that each one of the components (a) and (b) are present. However, it is generally useful to use a mixture of more than one components (a), for example from 2 to 100 components (a). In particular, oligomers are usually mixtures of components having different molecular weights. More than one components (b) can also advantageously be used, for example from 2 to 100 components (b). When more than one components (b) are used, they can have similar or different reactivities, in the latter case enabling stepwise polymerisation. It is also possible to add further components (a) and/or (b) at any stage after the polymerization has been started.

Oligomers in the sense of the invention are compounds obtainable by linking together from 2 to about 50, preferably from 3 to 20 ethylenically unsaturated units, which compounds still comprise at least one ethylenically unsaturated double bonds and usually have a molecular weight of from 150 to 5000 Da.

Ethylenically unsaturated, polymerizable monomers or oligomers are generally known radically polymerizable compounds having at least one ethylenically unsaturated double bond, including monomers, prepolymers, oligomers and copolymers of any thereof. Non-limiting examples of such monomers include:

ethylenically unsaturated polymerizable monomers selected from the group consisting of alkenes, conjugated dienes, styrenes, acrolein, vinyl acetate, vinylpyrrolidone, vinylimidazole, maleic anhydride, acrylic acid, acrylic acid derivatives, vinyl halides and vinylidene halides, such as ethylene, isoprene, 1,3-butadiene and α-$C_5$-$C_{18}$alkenes, styrene and styrenes substituted on the phenyl group by from one to three substituents selected from the group consisting of hydroxy, $C_1$-$C_4$alkoxy, e.g. methoxy or ethoxy, halogen, e.g. chlorine, amino and $C_1$-$C_4$alkyl, e.g. methyl or ethyl, such as methyl styrene, chloromethyl styrene, o-, m-, or p-hydroxystyrene;

unsaturated carboxylic acids such as acrylic acid, methacrylic acid, crotonic acid, itaconic acid, maleic acid, or fumaric acid and salts, esters and amides thereof, as well as unsaturated fatty acids such as linolenic acid and oleic acid, acrylic and methacrylic acid being preferred; such unsaturated carboxylic acids optionally being used in admixture with saturated di- or poly-carboxylic acids, such as malonic acid, succinic acid, glutaric acid, adipic acid, sebacic acid, 1,4-cyclohexane dicarboxylic acid, tetrachlorophthalic acid, tetrabromophthalic acid, phthalic anhydride, tetrahydrophthalic acid, isophthalic acid, terepthalic acid, trimellitic acid, heptanedicarboxylic acid, dodecanedicarboxylic acid orhexahydrophthalic acid;

unsaturated carboxylic acid esters derived from abovementioned unsaturated carboxylic acids and mixtures of unsaturated carboxylic acids, wherein the esters are for example alkyl esters such as methyl, ethyl, 2-chloroethyl, N-dimethylaminoethyl, n-butyl, isobutyl-, pentyl, hexyl, cyclohexyl, 2-ethylhexyl, octyl, isobornyl or [2-exobornyl] esters; benzyl esters; phenyl, benzyl or o-, m- and p-hydroxyphenyl esters; hydroxy alkyl esters such as 2-hydroxyethyl, 2-hydroxypropyl, 4-hydroxybutyl, 3,4-dihydroxybutyl or glycerol [1,2,3-propanetriol] esters; epoxy alkyl esters such as glycidyl, 2,3-epoxybutyl, 3,4-epoxy butyl, 2,3-epoxycyclohexyl or 10,11-epoxyundecyl esters; amino alkyl or mercapto alkyl esters; or polyfunctional esters as described below;

unsaturated carboxylic acid amides derived from abovementioned unsaturated carboxylic acids and mixtures of unsaturated carboxylic acids, wherein the amides groups may be similar as for above-mentioned esters, for example (meth)acryl amides or N-substituted (meth) acryl amides such as N-methylolacrylamide, N-methylolmethacrylamide, N-ethylacryamide, N-ethylmethacrylamide, N-hexylacrylamide, N-hexylmethacrylamide, N-cyclohexylacrylamide, N-cyclohexylmethacrylamide-, N-hydroxyethylacrylamide, N-phenylacrylamide, N-phenylmethacrylamide, N-benzylacrylamide, N-benzylmetacrylamide, N-nitrophenylacrylamide, N-nitrophenylmethacrylamide, N-ethyl-N-phenylacrylamide, N-ethyl-N-phenylmethacrylamide, N-(4-hydroxyphenyl)acrylamide, and N-(4-hydroxyphenyl)methacrylamide or IBMAA (N-isobutoxymethyl acrylamide, or amides with aliphatic polyvalent amines;

(Meth)acrylnitriles;

unsaturated acid anhydrides such as itaconic anhydride, maleic anhydride, 2,3-dimethyl maleic anhydride or 2-chloromaleic anhydride;

vinyl ethers such as isobutyl vinyl ether, ethyl vinylether, 2-chloroethyl vinylether, hydroxyethyl vinylether, propyl vinylether, butyl vinylether, isobutyl vinyl ether, octyl vinylether or phenyl vinylether;

vinyl esters such as vinyl acetate, vinyl chloroacetate, vinyl butyrate and vinyl benzoate;

vinyl chloride or vinylidene chloride;

N-vinyl heterocyclic compounds, such as N-vinylpyrrolidone or suitably substituted vinylpyrrolidones, N-vinylcarbazol or 4-vinylpyridine;

diacrylate esters such as 1,6-hexane diol diacrylate (HDDA), ethylene glycol diacrylate, propylene glycol diacrylate, tripropylene glycol diacrylate, neopentyl glycol diacrylate, hexamethylene glycol diacrylate and bisphenol A diacrylate;

divinylbenzene, divinyl succinate, diallyl phthalate, triallyl phosphate, triallyl isocyanurate or tris(2-acryloylethyl) isocyanurate;

esters of multifunctional alcohols, for example aromatic polyols such as hydroquinone, 4,4'-dihydroxydiphenyl, 2,2-di(4-hydroxyphenyl)propane, novolaks or resols, or, especially, aliphatic and cycloaliphatic polyols including e.g. alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol, these polyols being optionally partially or fully esterified by one or by different unsaturated carboxylic acid(s), it being possible for the free hydroxyl groups in partial esters to be modified, for example etherified, or esterified by other carboxylic acids; or esters of polyepoxides based on these polyols, especially from aromatic polyols and epichlorohydrin, as well as polymers and copolymers that contain hydroxyl groups in the polymer chain or in side groups, such as polyvinyl alcohol and copolymers thereof, polymethacrylic acid hydroxyalkyl esters or copolymers thereof, or oligoesters having hydroxyl terminal groups; such as trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tri pentaerythritol octaacrylate, pentaerythritol dimethacrylate, pentaerythritol trimethacrylate, dipentaerythritol dimethacrylate, dipentaerythritol tetramethacrylate, tri pentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates or methacrylates, glycerol di- or tri-acrylate, 1,4-cyclohexane diacrylate, bisacrylates or bismethacrylates of polyethylene glycol having a molecular weight of from 200 to 1500 Da, dipropylene glycol diacrylate, tripropylene glycol diacrylate, glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate or neopentyl glycol propoxylate diacrylate;

non limiting examples of higher molecular weight (oligomeric) polyunsaturated compounds (also known as prepolymers) are esters of ethylenically unsaturated mono- or poly-functional carboxylic acids as described above and polyols or polyepoxides; polymers having ethylenically unsaturated groups in the chain or in side groups, such as unsaturated polyesters, polyamides and polyurethanes and copolymers thereof; alkyd resins; polybutadiene or butadiene copolymers, polyisoprene or isoprene copolymers, polymers or copolymers having (meth)acrylic groups in side chains such as methacrylated urethanes or also mixtures of one or more such polymers; or aminoacrylates;

or mixtures of any number of any thereof in any proportions, independently from their functionality, optionally in combination with further reactive components such as so-called aminoacrylates, that is, oligomers based on acrylates which has been modified by reaction with primary or secondary amines, as described, for example, by Gaske in U.S. Pat. No. 3,844,916, by Weiss et al. in EP 0 280 222, by Meixner et al. in U.S. Pat. No. 5,482,649 or by Reich et al. in U.S. Pat. No. 5,734,002. Commercial aminoacrylates are, for example, Ebecryl® 80, Ebecryl® 81, Ebecryl® 83, Ebecryl® P115, Ebecryl® 7100 (UCB Chemicals), Laromer® PO 83F, Laromer® PO 84F, Laromer® PO 94F (BASF), Photomer® 4775 F, Photomer® 4967 F (Cognis), CN501™, CN503™ or CN550™ (Cray Valley).

Polymers, preferably coatings, may advantageously be prepared from the instant compositions. To prepare a polymer, preferably a coating, the components (a) and (b) of the formulation and optionally colourants and/or additives are applied uniformly to a substrate by means of known coating techniques, for example by spincoating, immersion, knife coating, curtain pouring, brush application or spraying, especially by electrostatic spraying and reverse-roll coating, or also by electrophoretic deposition. The quantity applied (coating thickness) and the nature of the substrate (layer support) are dependent on the desired field of application. The coating thicknesses are generally comprised in the range of from 0.1 µm to more than 300 µm, though the coatings may if desired also be thicker, for example 1-5 mm.

The wet coatings are then cured by polymerization as described below.

The instant coatings should be understood also to comprise printing inks (as long as wet) and prints (dry after curing).

Depending on their specific composition, the coatings can be applied as printing inks, liquid coatings, powder coatings or gelcoats on any desired substrate. Suitable are substrates of any kind, for example wood, textiles, paper, ceramics, glass, glass fibres, plastics such as polyester, polyethylene terephthalate, polyolefins or cellulose acetate, especially in the form of films, and also metals such as Al, Cu, Ni, Fe, Zn, Mg, Co, GaAs, Si or $SiO_2$, to which there can be applied a protective or decorative layer, if desired by image-wise exposure and/or on an already existing coating, such as a primer.

The above-described compositions may further comprise customary additives, which may, as an alternative, also be added after the polymerization. Such additives can be added in usual small amounts, e.g. UV-absorbers or light stabilizers, e.g. compounds selected from the group consisting of hydroxyphenylbenzotriazoles, hydroxyphenylbenzophenones, oxalamides and hydroxyphenyl-s-triazines. Particularly suitable light stabilizers are those selected from the group consisting of sterically hindered amines (HALS), e.g. of the 2-(2-hydroxyphenyl)-1,3,5-triazine or 2-hydroxyphenyl-2H-benzotriazole type. Examples of light stabilizers of the 2-(2-hydroxyphenyl)-1,3,5-triazine type are known for example from U.S. Pat. No. 4,619,956, EP 0 434 608, U.S. Pat. No. 5,198,498, U.S. Pat. No. 5,322,868, U.S. Pat. No. 5,369,140, U.S. Pat. No. 5,298,067, WO-94/18 278, EP 0 704 437, GB-2,297,091 or WO-96/28 431.

The preferred colourants are pigments, especially organic pigments such as those listed in the Colour Index.

The compositions may further comprise other customary additives, e.g. fillers such as calcium carbonate, silicates, glass or glass fibre material, talcum, kaolin, mica, barium sulphate, metal oxides and hydroxides, carbon black, graphite, pulverized wood and pulverized or fibrous material from other natural products, synthetic fibres, plasticizers, lubricants, emulsifiers, pigments, fluidizers, catalysts, optical brighteners, flame retardants, antistatics or blowing agents.

Hence, the invention also pertains to the use of the instant compounds of formula (I) to generate radicals in reactions triggered by the presence of radicals, as well as a process for preparing polymeric matter, preferably in the form of coatings, by using compositions comprising compounds of formula (I).

The invention further provides a process for preparing the above-described oligomer, cooligomer, polymer or copolymer by free-radical polymerization using the above-described compounds of formula (I).

Free radical polymerization includes thermal polymerisation, including thermal curing, IR-curing and NIR-curing, and/or UV polymerisation. Thermal curing refers to the application of convection heat or IR- or NIR-radiation after the mixture has been applied to the substrate. In case of powder coatings, the adhered powder coating is first melted to form a surface layer preferably by convection heat. Convection heat usually leads to temperatures of from 50° C. to 250° C.

The NIR radiation used in the process according to the invention is short-wave infrared radiation in the wavelength range from about 750 nm to about 1500 nm, preferably from 750 nm to 1200 nm. Radiation sources for NIR radiation include, for example, conventional NIR radiation emitters, which are available commercially (for example, from Adphos).

The IR radiation used in the process according to the invention is medium wave radiation in the wave length range from about 1500 nm to about 3000 nm and/or longer-wave infrared radiation in the wave length range above 3000 nm. Such IR radiation emitters are available commercially, too (for example, from Heraeus).

The invention further provides a generally applicable, inventive process for the controlled degradation of polyolefins wherein the compounds of formula (I) are used to lower the molecular weight of polyolefins, preferably polypropylene, propylene copolymers or polypropylene blends.

In the instant degradation process, the compounds of formula (I) are adequately incorporated into the polyolefin to be degraded in concentrations of from about 0.001 to 5.0% by weight, preferably from 0.01 to 2.0% by weight and particularly preferably from 0.02 to 1.0% by weight, based on the total weight of the polyolefin to be degraded. Such amounts are effective for desirably reducing the molecular weight. The compounds of formula (I) can be added as individual compounds or as mixtures to the polyolefin to be degraded.

The polyolefin-type polymers to be degraded encompass in particular propylene homopolymers, propylene copolymers and polypropylene blends. Propylene copolymers may be build up from olefin mixtures comprising propylene and various proportions of comonomers, generally up to 90% by weight, preferably up to 50% by weight of comonomers, based on the olefin mixture. Examples of comonomers are olefins such as 1-olefins, e.g. ethylene, 1-butene, isobutylene, 1-pentene, 1-hexene, 1-heptene or 1-octene; cycloolefins, e.g. cyclopentene, cyclohexene, norbornene or ethylidenenorborne; dienes such as butadiene, isoprene, 1,4-hexadiene, cyclopentadiene, dicyclopentadiene or norbornadiene; acrylic acid derivatives; or unsaturated carboxylic anhydrides such as maleic anhydride.

Polypropylene blends which can be used are mixtures of polypropylene with polyolefins. Examples are blends of polypropylene with polyethylenes such as high density polyethylene (HDPE), high molecular weight high density polyethylene (HMW HDPE), ultra high molecular weight high density polyethylene (UHMW HDPE), medium density polyethylene (MDPE), low density polyethylene (LDPE), linear low density polyethylene (LLDPE), branched low density polyethylene (BLDPE) or ethylene-propylene-diene terpolymers (EPDM) containing small proportions of diene.

Incorporation into the polymers can be carried out, for example, by mixing the compounds of formula (I) or mixtures thereof and, if desired, further additives into the polymers using the methods customary in process technology.

Incorporation can, alternatively, also be carried out at temperatures which do not yet cause decomposition of the polymers (latent compound). The polymers prepared in this way can subsequently be heated a second time and subjected to an elevated temperature for a sufficient period of time so that the desired polymer degradation occurs.

Preferably, $R_1$, $R_2$, $R_3$ and $R_4$ are each independently from the other $C_1$-$C_6A_{LK}$yl, especially methyl or ethyl, and $R_5$ and $R_6$ are each independently from the other H or $C_1$-$C_6A_{LK}$yl, especially H, methyl or ethyl. Most preferred, the total number of C atoms in $R_1$, $R_2$, $R_3$ and $R_4$ is at least 5, preferably at least 6. More preferably, these preferred scopes may be combined with other preferences disclosed herein, such as n=1 or n=2.

Further preferred are the triazenes of formulae

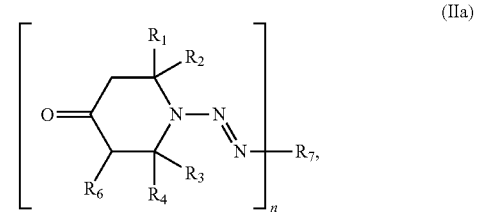

(IIa)

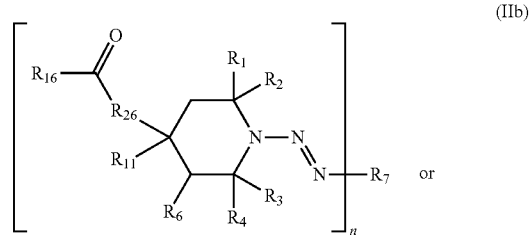

(IIb)

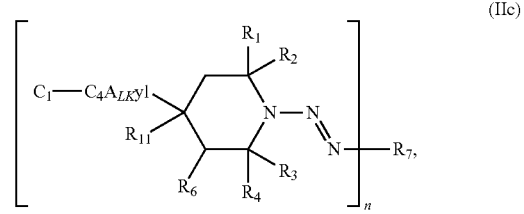

(IIc)

wherein
$R_1$, $R_2$, $R_3$ and $R_4$ are each independently from the other $C_1$-$C_4A_{LK}$yl;
$R_6$ and $R_{11}$ are each independently from the other H or $C_1$-$C_4A_{LK}$yl;
$R_7$ is $C_6$-$C_{14}$aryl or $C_1$-$C_{12}$heteroaryl;
$R_{16}$ is H, $R_{18}$, $OR_{18}$, $NR_{18}R_{19}$, $R_{21}$—$COOR_{20}$, $R_{21}$—$CON(R_{20})R_{27}$, $R_{22}$(—$COOR_{20}$)—$COOR_{23}$ or $R_{22}$(—$CON(R_{20})R_{27}$)—$CON(R_{23})R_{28}$;
$R_{18}$ and $R_{19}$ are each independently from the other $C_1$-$C_{36}A_{LK}$yl, $C_2$-$C_{54}A_{LK}$enyl, $C_6$-$C_{14}$aryl, $C_7$-$C_{46}arA_{LK}$yl or $C_2$-$C_{36}A_{LK}$enylene-$C_6$-$C_{10}$aryl; or $R_{18}$ and $R_{19}$ are together $C_2$-$C_{36}A_{LK}$ylene or $C_2$-$C_{54}A_{LK}$enylene which is uninterrupted or once or twice interrupted by —O—, —NH— and/or —N($C_1$-$C_4A_{LK}$yl)-, thus forming a preferably 5- or 6-membered ring with the N-atom to which they are attached;
each $R_{20}$ or $R_{23}$ stands for H, $R_{18}$, $OR_{18}$, $NR_{18}R_{19}$, $COOR_{20}$, $R_{21}$—$COOR_{20}$, $R_{22}$(—$COOR_{20}$)—$COOR_{23}$ or

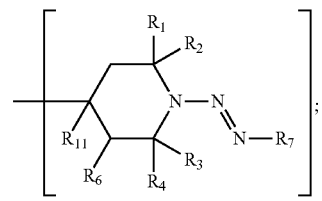

$R_{21}$ is $C_1$-$C_{12}A_{LK}$ylene, $C_2$-$C_{12}A_{LK}$enylene, $C_6$-$C_{10}$arylene or $C_2$-$C_{12}A_{LK}$enylene-$C_6$-$C_{10}$arylene;
$R_{22}$ is $C_1$-$C_{12}A_{LK}$antriyl, $C_2$-$C_{12}A_{LK}$entriyl, benzotriyl, $C_7$-$C_{18}$benzoA$_{LK}$antriyl, $C_2$-$C_{12}A_{LK}$antriyl-$C_6$-$C_{10}$arylene, $C_2$-$C_{12}A_{LK}$enylene-benzotriyl or $C_2$-$C_{12}A_{LK}$entriyl-$C_6$-$C_{10}$arylene;
$R_{26}$ is O, NH or N($C_1$-$C_4A_{LK}$yl);

$R_{27}$ and $R_{28}$ are each independently from the other H, $C_1$-$C_{24}$alkyl, $C_7$-$C_{24}$aralkyl, $C_6$-$C_{24}$aryl or $C_1$-$C_{24}$heteroaryl;
n is 1 or 2; and
$A_{LK}$ is an unsubstituted or substituted hydrocarbon residue as defined above.

In formula (IIc), $R_{11}$ is preferably bound to $C_1$-$C_4 A_{LK}$yl in geminal position, thus forming a spiro compound which optionally may form further fused or spiro rings when $R_{11}$ is cyclic.

Most preferred are the triazenes of formulae (IIa), (IIb) or (IIc), wherein $R_1$, $R_2$, $R_3$ and $R_4$ are independently from each other methyl or ethyl, $R_6$ is H or methyl and n is 1 or 2.

The above-mentioned preferred compounds are of course also preferred as components of the instant compositions and for use in the instant polymerization and degradation processes or as flame retardants.

The triazenes of formula (I) are novel with only the following few exceptions:

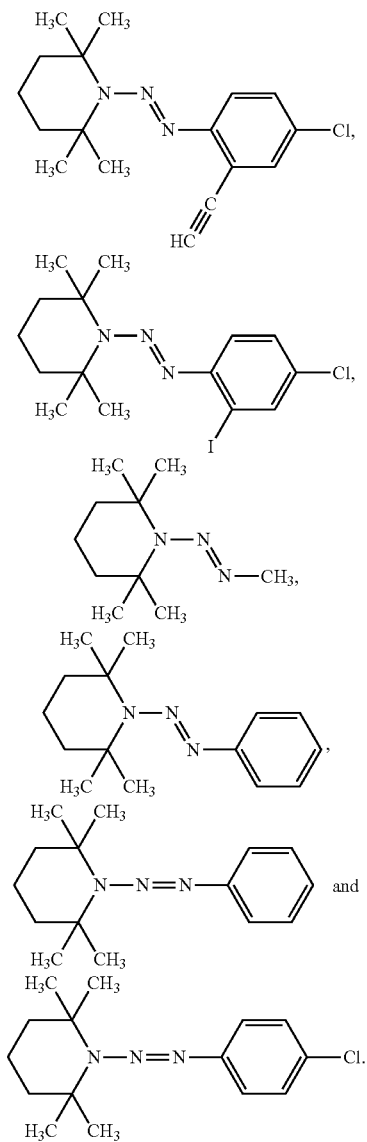

Hence, the invention also pertains to a compound of formula (I), with the proviso that the triazene of formula (I) is not of formula

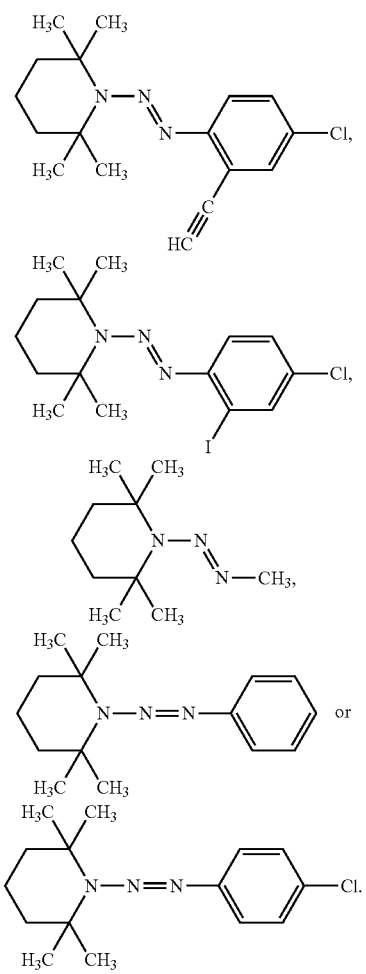

Though the compounds excluded by above proviso are neither novel nor preferred, they can also be used as polymerization or degradation initiators according to the invention.

The compounds of formulae (I), (IIa), (IIb) or (IIc) can also very advantageously be used in replacement for the sterically hindered N-acyloxyamines and N-substituted imides of WO 2001/90 113A1, WO 2004/081 100A1 and WO 2006/051 047A1, the entire contents of which are incorporated herein by reference, according to the procedures disclosed therein.

The examples which follow illustrate the invention, without limiting it ("%" are by weight where not otherwise specified):

EXAMPLE 1

9.31 g Aniline is added to a mixture of 50 g ice and 29.4 ml aqueous HCl (32% w/w). Then, a solution of 6.90 g $NaNO_2$ in 30 ml water is slowly added while keeping the temperature between −5 and 0° C. To this solution, a cold (−5° C.) solution of 15.7 g 2,2,6,6-tetramethyl-4-hydroxypiperidine in 30 ml water and 9.8 ml aqueous HCl (32% w/w) and a cold solution of 16 g NaOH in 40 ml water are slowly added sequentially while keeping the temperature in the range from −5 to 0° C. The thick brown suspension is allowed to warm up to 23° C. and is then diluted with 100 ml dichloromethane. The organic phase is separated, evaporated and chromatographed on silica gel with hexane-ethylacetate (2:1) to afford 17.4 g of 2,2,6,6-tetramethyl-1-phenyldiazenyl-piperidin-4-ol as a slightly yellow oil which solidifies on standing. A sample of this material is recrystallized from dichloromethane-hexane to afford light yellow solid, m.p. 68-70° C.

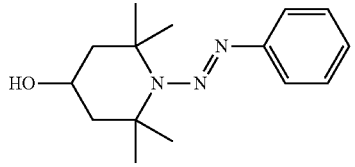 [SMILES: CC1(C)CC(O)CC(C)(C)N1/N=N/c1ccccc1]

MS: M$^+$=261 (C$_{15}$H$_{23}$N$_3$O=261.37);
$^1$H-NMR (CDCl$_3$, 300 MHz), δ (ppm): 7.4-7.1 (m, 5 ArH), 4.2-4.1 (m, 1H), 2.03-1.4 (m, 4H), 1.72 s (2×CH$_3$), 1.43 (s, 2×CH$_3$).

EXAMPLE 2

2.15 ml Benzoylchloride are dropwise added to a solution of 4.42 g 2,2,6,6-tetramethyl-1-phenyldiazenyl-piperidin-4-ol (see example 1) and 0.1 g 4-dimethylaminopyridine in 35 ml pyridine. The resulting mixture is stirred 4 hours at 23° C., then diluted with 300 ml ice-water. The precipitate is filtered off and recrystallized twice from methanol to afford 4.43 g of benzoic acid 2,2,6,6-tetramethyl-1-phenyldiazenyl-piperidin-4-yl ester as an off-white solid, m.p. 89-91° C.

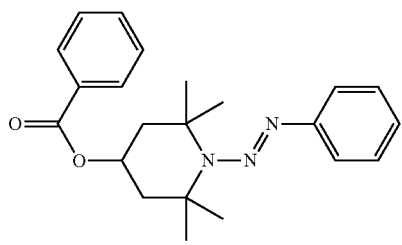 [SMILES: CC1(C)CC(OC(=O)c2ccccc2)CC(C)(C)N1/N=N/c1ccccc1]

$^1$H-NMR (CDCl$_3$, 300 MHz), δ (ppm): 8.067-8.05 (d, J=5.1 Hz, 1 ArH), 7.6-7.05 (m, 8 ArH), 5.5-5.4 (m, 1H), 2.23-1.95 (m, 4H), 1.74 (s, 2×CH$_3$), 1.54 (s, 2×CH$_3$).

EXAMPLE 3

9.6 g Benzenediazonium tetrafluoroborate are added to a cold (0° C.) solution of 18.3 g 2,6-diethyl-2,3,6-trimethyl-piperidine (prepared as described in WO 2000/046 202) in 100 ml dichloromethane. The solution is allowed to warm to 23° C. within 10 hours, then further stirred at 23° C. for 30 hours, washed with 1M-HCl (2×100 ml) and evaporated. The brown oil is chromatographed on silica gel with hexane-ethylacetate (98:2) to afford 2.48 g of 2,6-diethyl-2,3,6-trimethyl-piperidin-1-yl)-phenyl-diazene as a slightly yellow oil.

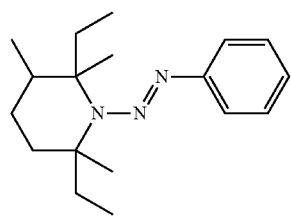 [SMILES: CCC1(C)CCC(C)C(C)(CC)N1/N=N/c1ccccc1]

GC-MS: 4 closely spaced peaks each with M$^+$=287 (C$_{18}$H$_{29}$N$_3$=287.45);
$^1$H-NMR (CDCl$_3$, 300 MHz), δ (ppm): 7.4-7.0 (m, 5 ArH), 2.9-0.6 (m, 24H).

EXAMPLE 4

A mixture of concentrated HCl (30 ml, 32%) and water (30 ml) is charged into 100 ml three necked round bottomed flask followed by addition of p-Toluidine (10 g, 0.0.093 mol). The mixture is cooled to 0 to 5° C. and solution of sodium nitrite (11.2 g, 0.16 mol) in water (15 ml) is added into it while maintaining the temperature at 0 to 5° C. This reaction mixture is then slowly added into a solution of 2,2,6,6-tetramethyl-4-hydroxypiperidine (69 g, 0.44 mol) in acetonitrile (2000 ml) and the mixture is stirred at 0 to –5° C. for 1 h. The reaction mass is filtered and the mother liquor evaporated to dryness at 40° C. The solid residue is extracted with cyclohexane (500 ml) and diethyl ether (800 ml). The extracts are decolorized with charcoal (25 g) filtered through bed of celite and concentrated at 25 C to afford 6.0 g of 2,2,6,6-Tetramethyl-1-(p-tolyl-diazenyl)-piperidine-4-ol as a yellow solid, m.p. 85-86° C.

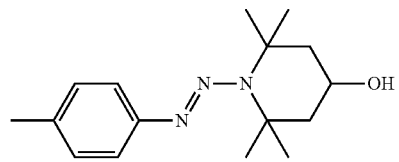

$^1$HNMR (ppm, d$_6$-DMSO; 7.19 (d, J=8.4, 2H), 7.12 (d, J=8.4, 2H), 4.7 (broad s, 1H), 3.93 (broad t, 1H), 2.26 (s, 3H), 1.90 (m, 2H), 1.59-1.53 (s, 8H), 1.35 (s, 6H).
MS (275, M$^+$)

EXAMPLE 5

A mixture of concentrated HCl (15 ml, 32%) and water (15 ml) is charged into 100 ml three necked round bottomed flask followed by addition of 4-nitro-aniline (5 g, 0.04 mol). The mixture is cooled to 0 to 5° C. and solution of sodium nitrite (4.14 g, 0.06 mol) in water (5 ml) is added into it while maintaining temperature 0 to 5° C. This reaction mixture is then slowly added into a solution of sodium tetrafluoroborate (6.6 g, 0.06 mol) in water (60 ml) at 0 to 5° C. The resulting solution of diazonium tetrafluoroborate salt is then added to solution of 2,2,6,6-tetramethyl-4-hydroxypiperdine (25.1 g, 0.16 mol) in acetonitrile (1000 ml)) and the mixture is stirred at 0 to –5° C. for 1 h. This reaction mixture filtered and mother liquor is evaporated to dryness at 40° C. The residue is extracted with diethyl ether (200 ml) the extract is decolorized with charcoal (50 g), filtered through bed of celite and concentrated to dryness to afford 0.56 g of 2,2,6,6-Tetramethyl-1-(4-nitrophenyldiazenyl)-piperidin-4-ol as a yellow solid, m.p. 108-110° C.

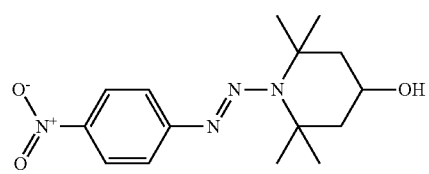

¹HNMR (ppm, d₆-DMSO); 8.20 (d, J=8.8, 2H), 7.47 (d, J=8.8, 2H), 4.80 (s, 1H), 4.14 (broad t, 1H), 1.98 (m, 2H), 1.62 (brad s, 8H), 1.42 (s, 6H).

MS (306, M⁺)

EXAMPLE 6

50 g crushed ice are added to a solution of 2-bromoaniline in 4 ml THF and 4 ml aqueous HCl (32% w/w). The yellow suspension is diazotized at −5° C. by treatment with a solution of 1.1 g sodium nitrite in 10 ml water. After 3 h, a solution of 2.76 g 2,2,6,6-tetramethyl-4-hydroxypiperidine in 1.5 ml aqueous HCl (32% w/w) and 1 ml THF are added dropwise to the thick yellow suspension at −3° C. Addition of water (ca. 20 ml) is necessary to keep the mixture well stirrable. The reaction mixture is then neutralized by adding dropwise 8.8 ml of aqueous sodium hydroxide (30% w/w) and 4 ml THF between 0 and 2° C. The brownish mixture is extracted with ethyl acetate. The organic phase is separated, evaporated and chromatographed on silica gel with hexane-ethylacetate (3:1), yielding 1.11 g of 1-(2-bromophenyl-diazenyl)-2,2,6,6-tetramethyl-piperidin-4-ol as a red-brown solid, m.p. 81° C.

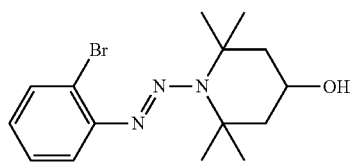 [SMILES: CC1(C)CC(O)CC(C)(C)N1/N=N/c1ccccc1Br]

MS: M⁺=340/342 ($C_{15}H_{22}Br\ N_3O$=340.26);
¹H-NMR (CDCl₃, 300 MHz), δ (ppm): 7.6-7.0 (m, 4 ArH), 4.2-4.1 (m, 1H), 2.0-1.3 (m, 4H), 1.73 s (2×CH₃), 1.48 (s, 2×CH₃).

EXAMPLE 101

Polymerization of n-butyl acrylate

Materials and Methods

All solvents and monomers are distilled under argon or under reduced pressure via a Vigreux column shortly before use.

All reaction mixtures are freed of oxygen by purging with argon using the freeze/thaw technique and subsequently maintained under argon gas prior to the polymerization.

The reactants are in the form of a clear homogeneous solution before commencement of the polymerization reaction.

The monomer conversion is determined via ¹H-NMR by integrating the signals of the polymer and unreacted monomer.

The polymers are characterized by GPC (gel permeation chromatography).

GPC: a two-piston production model pump Rheos® 4000 from Flux Instruments (represented by Ercatech A G, Bern, Switzerland) is used. The pump output is 1 ml/min. The chromatography is carried out on two Plgel 5 μm mixed-C columns (Polymer Instruments, Shropshire UK) connected in series at 40° C. in THF. These columns are calibrated using polystyrene having $M_n$ values in the range from 200 to 2 000 000. The fractions are measured using an RI detector ERC-7515A (Ercatech) at 30° C.

130.7 mg of the compound according to example 1 and 6.41 g of n-butyl acrylate are placed in a 50 ml three-necked round-bottom flask provided with thermometer, condenser and magnetic stirrer and the mixture is degassed. The flask is immersed into an oil bath kept at 120° C. A rapid exothermic polymerization occurs. The clear solution is heated to 120° C. for 5 hours under argon, then cooled to 23° C. to afford poly-n-butylacrylate as a light yellow, hard resin. The polymer is insoluble in chloroform or tetrahydrofuran, indicating a quantitative polymerization though characterization via NMR or GPC is impracticable.

EXAMPLES 102-103

It is proceeded as in Example 101, with the difference that the compound according to example 1 is replaced by the compounds according to Examples 2 and 3, respectively.

EXAMPLE 104

Polymerization of a Coating Composition

The following unsaturated polymerizable composition is used (w/w %)

| | |
|---|---|
| Urethane-acrylate (Ebecryl 4858, UCB Chemicals/Cytec) | 50% |
| 1,6-Hexandiol diacrylate (UCB Chemicals/Cytec) | 30% |
| Tripropylene glycol diacrylate (UCB Chemicals/Cytec) | 20% |

1% of a compound (see Table 1) is dissolved in this composition and the resulting mixture is submitted to Differential scanning calorimetry (DSC) measurement. The activity of the tested compound is manifested by the exothermic curing reaction which is characterized by the Onset, Peak and Endset temperatures as well as the amount of heat liberated (exothermy).

The Following DSC Parameters are Used:

Apparatus: DSC 30 (Mettler)

Temperature Gradient: 5° C./Min

Temperature Range: 30-300° C.

Measurement under Nitrogen, flow rate 5 ml/Min

Sample amount: approx. 10 mg compound in an aluminum cup

The results summarized in the Table 1 show that no curing occurs with the blank formulation but that distinct exothemic curing is observed with the examples of the inventive compounds.

TABLE 1

Table 1: DSC evaluation

| Compound from example | Onset [° C.] | Peak [° C.] | Endset [° C.] | Exothermy [J/g] |
|---|---|---|---|---|
| — (blank) | no | no | no | 0 |
| 1 | 108.46 | 111.70 | 113.71 | 68.92 |
| 4 | 113.8 | 133.89 | 158.75 | 350.47 |

The invention claimed is:
1. A composition, comprising:
   (a) an ethylenically unsaturated, polymerizable monomer or oligomer; and
   (b) an effective, thermally or actinically radicals-generating amount of a compound of formula (I):

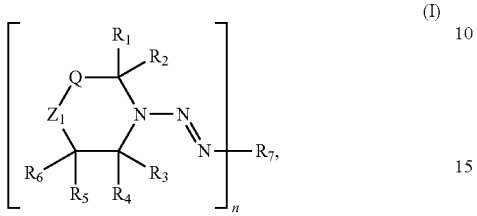

wherein:
Q is a direct bond or a bivalent radical —$(CR_8R_9)$—;
$Z_1$ is —O—, —$NR_{10}$—, —$CH_2$—, —$(CR_{11}R_{12})$— or —C(=O)—;
$R_1$ and $R_2$ are each, independently from the other, $C_1$-$C_6A_{LK}$yl, or $R_1$ and $R_2$ are together $C_4$-$C_7A_{LK}$ylene thus forming a cyclic group with the C-atom to which they are attached;
$R_3$ and $R_4$ are each, independently from the other, $C_1$-$C_6A_{LK}$yl, or $R_3$ and $R_4$ are together $C_4$-$C_7A_{LK}$ylene thus forming a cyclic group with the C-atom to which they are attached;
$R_5$ and $R_6$ are each, independently from the other, H, $C_1$-$C_6A_{LK}$yl, $C_6$-$C_{10}$aryl or $C_7$-$C_{12}$ar$A_{LK}$yl, or $R_5$ and $R_6$ are together oxygen thus forming a carbonyl group together with the C-atom to which they are attached;
$R_7$ is $C_6$-$C_{24}$aryl, $C_7$-$C_{24}$ar$A_{LK}$yl, $C_1$-$C_{24}$heteroaryl or $C_2$-$C_{24}$heteroar$A_{LK}$yl;
$R_8$ and $R_9$ are each, independently from the other, H or $C_1$-$C_6A_{LK}$yl;
$R_{10}$ is hydrogen, $C_1$-$C_6A_{LK}$yl, $C_6$-$C_{10}$aryl or —O—C(=O)—$R_{13}$;
$R_{11}$ is hydrogen or $C_1$-$C_6A_{LK}$yl;
$R_{12}$ is $R_{14}$, C(=O)—$R_{14}$, CN, OH, $OR_{14}$, $NH_2$, $NHR_{14}$, $NR_{14}R_{15}$, O—C(=O)—$R_{16}$, NH—C(=O)—$R_{16}$ or $NR_{14}$—C(=O)—$R_{16}$;
or $R_{11}$ and $R_{12}$ are together $C_2$-$C_{20}A_{LK}$ylene, which is uninterrupted or once or twice interrupted by —O— and/or —$NR_{17}$— thus forming a ring with the C-atom to which they are attached, which $C_2$-$C_{20}A_{LK}$ylene can optionally be annelated with benzo or naphtho, and which $C_2$-$C_{20}A_{LK}$ylene is further unsubstituted or substituted by 1 or 2, identical or different, groups —OH or —O—C(=O)—$R_{13}$;
$R_{13}$ is H, $R_{18}$, $OR_{18}$, $NR_{18}R_{19}$, $COOR_{20}$, $R_{21}$—$COOR_{20}$ or $R_{22}$(—$COOR_{20}$)—$COOR_{23}$;
$R_{14}$ and $R_{15}$ are each, independently from the other, $C_1$-$C_6A_{LK}$yl, $C_7$-$C_{12}$ar$A_{LK}$yl or $C_6$-$C_{10}$aryl, or $R_{14}$ and $R_{15}$ are together $C_2$-$C_6A_{LK}$ylene, which is uninterrupted or once or twice interrupted by —O— and/or —$NR_{17}$— thus forming a ring with the N-atom to which they are attached;
$R_{16}$ is H, $R_{18}$, $OR_{18}$, $NR_{18}R_{19}$, $COOR_{20}$, $R_{21}$—$COOR_{20}$ or $R_{22}$(—$COOR_{20}$)—$COOR_{23}$;
$R_{17}$ is H or $C_1$-$C_6A_{LK}$yl;
$R_{18}$ and $R_{19}$ are each, independently from the other, $C_1$-$C_{36}A_{LK}$yl, $C_2$-$C_{54}A_{LK}$enyl, $C_2$-$C_{24}A_{LK}$inyl, $C_6$-$C_{10}$aryl, $C_7$-$C_{46}$ar$A_{LK}$yl or $C_2$-$C_{36}A_{LK}$enylene-$C_6$-$C_{10}$aryl, or $R_{18}$ and $R_{19}$ are together $C_2$-$C_{36}A_{LK}$ylene or $C_2$-$C_{54}A_{LK}$enylene, which is uninterrupted or once or twice interrupted by —O— and/or —$NR_{17}$— thus forming a ring with the N-atom to which they are attached;
$R_{21}$ is $C_1$-$C_{12}A_{LK}$ylene, $C_2$-$C_{12}A_{LK}$enylene, $C_2$-$C_{12}A_{LK}$inylene, $C_6$-$C_{10}$arylene, $C_7$-$C_{18}$ar$A_{LK}$ylene or $C_2$-$C_{18}A_{LK}$enylene-$C_6$-$C_{10}$arylene;
$R_{22}$ is $C_1$-$C_{12}A_{LK}$antriyl, $C_2$-$C_{12}A_{LK}$entriyl, $C_3$-$C_{12}A_{LK}$intriyl, benzotriyl, naphthotriyl, $C_7$-$C_{18}$-benzo$A_{LK}$antriyl, $C_{11}$-$C_{22}$naphtho$A_{LK}$antriyl, $C_2$-$C_{12}A_{LK}$antriyl-$C_6$-$C_{10}$arylene, $C_2$-$C_{12}A_{LK}$enylene-benzotriyl, $C_2$-$C_{12}A_{LK}$enylene-naphthotriyl or $C_2$-$C_{12}A_{LK}$entriyl-$C_6$-$C_{10}$arylene;
each $R_{20}$ or $R_{23}$ stands, independently from any other $R_1$, $R_2$, $R_3$, $R_4$, $R_5$, $R_6$, $R_7$, $R_{11}$, $R_{18}$, $R_{19}$, $R_{20}$ or $R_{23}$, for H, $R_{18}$, $OR_{18}$, $NR_{18}R_{19}$, $COOR_{20}$, $R_{21}$—$COOR_{20}$, $R_{22}$(—$COOR_{20}$)—$COOR_{23}$ or

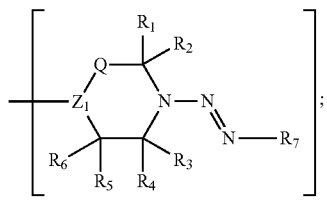

$A_{LK}$ stands for a linear or once or several times branched, and/or mono- or polycyclic, hydrocarbon residue including spiro residues, wherein one or more —$CH_2$— groups may be replaced by —S— or —NH—, one or more

groups may be replaced by

and/or one or more non-adjacent —$CH_2$— groups may be replaced by —O—;
each hydrocarbon residue, $A_{LK}$, in $R_1$, $R_2$, $R_3$, $R_4$, $R_5$, $R_6$, $R_7$, $R_8$, $R_9$, $R_{10}$, $R_{11}$, $R_{14}$, $R_{15}$, $R_{17}$, $R_{18}$, $R_{19}$, $R_{21}$ and $R_{22}$ is, independently from all others, unsubstituted or substituted by one or more identical or different substituents selected from the group consisting of Br, Cl, F, I, $NO_2$, $OR_{24}$, $SR_{24}$, SCN, CN, $N(R_{24})R_{25}$, $N(R_{24})$—C(=O)—$R_{25}$, $N(R_{24})$—$COOR_{25}$, $N(COR_{24})COR_{25}$, $COOR_{24}$,

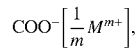

$COR_{24}$, O—C(=O)$R_{24}$, C(=O)$NR_{24}R_{25}$, O—C(=O)$NR_{24}R_{25}$,

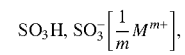

$SO_2NR_{24}R_{25}$, $S(=O)R_{24}$, $SO_2R_{24}$ and $P(=O)(OR_{24})OR_{25}$;

$R_{24}$ and $R_{25}$ are each, independently from any other, H, $C_1$-$C_{18}$alkyl, $C_7$-$C_{18}$aralkyl, $C_6$-$C_{24}$aryl or $C_1$-$C_{24}$heteroaryl, or $R_{24}$ and $R_{25}$ are each, independently from any other, H, $C_1$-$C_{18}$alkyl, $C_7$-$C_{18}$aralkyl, $C_6$-$C_{24}$aryl or $C_1$-$C_{24}$heteroaryl and $R_{24}$ and $R_{25}$ are additionally bound together through a direct bond or bridged over a O, S, NH, N—$C_1$-$C_{18}$alkyl, N—$C_7$-$C_{18}$aralkyl, N—$C_6$-$C_{24}$aryl or N—$C_1$-$C_{24}$heteroaryl bridge;

$M^{m+}$ is an organic or inorganic cation;

m is 1, 2, 3 or 4; and n is 1, 2, 3 or 4.

2. A composition, comprising:
(a) an ethylenically unsaturated, polymerizable monomer or oligomer; and
(b) an effective, thermally or actinically radicals-generating amount of a compound of formula (I):

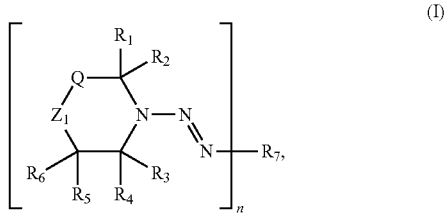

wherein:

Q is a direct bond or a bivalent radical —$(CR_8R_9)$—;

$Z_1$ is —O—, —$NR_{10}$—, —$CH_2$—, —$(CR_{11}R_{12})$— or —$C(=O)$—;

$R_1$ and $R_2$ are each, independently from the other, $C_1$-$C_6A_{LK}$yl, or $R_1$ and $R_2$ are together $C_4$-$C_7A_{LK}$ylene thus forming a cyclic group with the C-atom to which they are attached;

$R_3$ and $R_4$ are each, independently from the other, $C_1$-$C_6A_{LK}$yl, or $R_3$ and $R_4$ are together $C_4$-$C_7A_{LK}$ylene thus forming a cyclic group with the C-atom to which they are attached;

$R_5$ and $R_6$ are each, independently from the other, H, $C_1$-$C_6A_{LK}$yl, $C_6$-$C_{10}$aryl or $C_7$-$C_{12}$ar$A_{LK}$yl, or $R_5$ and $R_6$ are together oxygen thus forming a carbonyl group together with the C-atom to which they are attached;

$R_7$ is $C_6$-$C_{24}$aryl, $C_7$-$C_{24}$ar$A_{LK}$yl, $C_1$-$C_{24}$heteroaryl or $C_2$-$C_{24}$heteroar$A_{LK}$yl;

$R_8$ and $R_9$ are each, independently from the other, H or $C_1$-$C_6A_{LK}$yl;

$R_{10}$ is hydrogen, $C_1$-$C_6A_{LK}$yl, $C_6$-$C_{10}$aryl or —O—C(=O)—$R_{13}$;

$R_{11}$ is hydrogen or $C_1$-$C_6A_{LK}$yl;

$R_{12}$ is $R_{14}$, C(=O)—$R_{14}$, CN, OH, $OR_{14}$, $NH_2$, $NHR_{14}$, $NR_{14}R_{15}$, O—C(=O)—$R_{16}$, NH—C(=O)—$R_{16}$ or $NR_{14}$—C(=O)—$R_{16}$;

or $R_{11}$ and $R_{12}$ are together $C_2$-$C_{20}A_{LK}$ylene, which is uninterrupted or once or twice interrupted by —O— and/or —$NR_{17}$— thus forming a ring with the C-atom to which they are attached, which $C_2$-$C_{20}A_{LK}$ylene can optionally be annelated with benzo or naphtho, and which $C_2$-$C_{20}A_{LK}$ylene is further unsubstituted or substituted by 1 or 2, identical or different, groups —OH or —O—C(=O)—$R_{13}$;

$R_{13}$ is H, $R_{18}$, $OR_{18}$, $NR_{18}R_{19}$, $COOR_{20}$, $R_{21}$—$COOR_{20}$ or $R_{22}$(—$COOR_{20}$)—$COOR_{23}$;

$R_{14}$ and $R_{15}$ are each, independently from the other, $C_1$-$C_6A_{LK}$yl, $C_7$-$C_{12}$ar$A_{LK}$yl or $C_6$-$C_{10}$aryl, or $R_{14}$ and $R_{15}$ are together $C_2$-$C_6A_{LK}$ylene, which is uninterrupted or once or twice interrupted by —O— and/or —$NR_{17}$— thus forming a ring with the N-atom to which they are attached;

$R_{16}$ is H, $R_{18}$, $OR_{18}$, $NR_{18}R_{19}$, $COOR_{20}$, $R_{21}$—$COOR_{20}$ or $R_{22}$(—$COOR_{20}$)—$COOR_{23}$;

$R_{17}$ is H or $C_1$-$C_6$ $A_{LK}$yl;

$R_{18}$ and $R_{19}$ are each, independently from the other, $C_1$-$C_{36}A_{LK}$yl, $C_2$-$C_{54}A_{LK}$enyl, $C_2$-$C_{24}A_{LK}$inyl, $C_6$-$C_{10}$aryl, $C_7$-$C_{46}$ar$A_{LK}$yl or $C_2$-$C_{36}A_{LK}$enylene-$C_6$-$C_{10}$aryl, or $R_{18}$ and $R_{19}$ are together $C_9$-$C_{36}A_{LK}$ylene or $C_2$-$C_{54}A_{LK}$enylene, which is uninterrupted or once or twice interrupted by —O— and/or —$NR_{17}$— thus forming a ring with the N-atom to which they are attached;

$R_{21}$ is $C_1$-$C_{12}A_{LK}$ylene, $C_2$-$C_{12}A_{LK}$enylene, $C_2$-$C_{12}A_{LK}$inylene, $C_6$-$C_{10}$arylene, $C_7$-$C_{18}$ar$A_{LK}$ylene or $C_2$-$C_{18}A_{LK}$enylene-$C_6$-$C_{10}$arylene;

$R_{22}$ is $C_1$-$C_{12}A_{LK}$antriyl, $C_2$-$C_{12}A_{LK}$antriyl, benzotriyl, naphthotriyl, $C_7$-$C_{18}$-benzo$A_{LK}$antriyl, $C_{11}$-$C_{22}$naphtho$A_{LK}$antriyl, $C_2$-$C_{12}A_{LK}$antriyl-$C_6$-$C_{10}$arylene, $C_2$-$C_{12}A_{LK}$enylene-benzotriyl, $C_2$-$C_{12}A_{LK}$enylene-naphthotriyl or $C_2$-$C_{12}A_{LK}$entriyl-$C_6$-$C_{10}$arylene;

each $R_{20}$ or $R_{23}$ stands, independently from any other $R_1$, $R_2$, $R_3$, $R_4$, $R_5$, $R_6$, $R_7$, $R_{11}$, $R_{18}$, $R_{19}$, $R_{20}$ or $R_{23}$, for H, $R_{18}$, $OR_{18}$, $NR_{18}R_{19}$, $COOR_{20}$, $R_{20}$—$COOR_{20}$, $R_{22}$(—$COOR_{20}$)—$COOR_{13}$ or

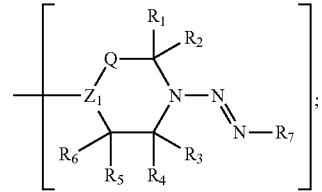

$A_{LK}$ stands for a linear or once or several times branched, and/or mono- or polycyclic, hydrocarbon residue including spiro residues, wherein one or more —$CH_2$— groups may be replaced by —S— or —NH—, one or more

groups may be replaced by

and/or one or more non-adjacent —$CH_2$— groups may be replaced by —O—;

each hydrocarbon residue, $A_{LK}$, $R_1$, $R_2$, $R_3$, $R_4$, $R_5$, $R_6$, $R_7$, $R_8$, $R_9$, $R_{10}$, $R_{11}$, $R_{14}$, $R_{15}$, $R_{17}$, $R_{18}$, $R_{19}$, $R_{21}$ and $R_{22}$ is, independently from all others, unsubstituted or substituted by one or more identical or different substituents selected from the group consisting of Br, Cl, F, I, $NO_2$, $OR_{24}$, $SR_{24}$, SCN, CN, $N(R_{24})R_{25}$, $N(R_{24})$—C(=O)—$R_{25}$, $N(R_{24})$—$COOR_{25}$, $N(COR_{24})COR_{25}$, $COOR_{24}$, $$COO^-\left[\frac{1}{m}M^{m+}\right],$$

$COR_{24}$, O—C(=O)$R_{24}$, C(=O)$NR_{24}R_{25}$, O—C(=O)$NR_{24}R_{25}$, $$SO_3H, SO_3^-\left[\frac{1}{m}M^{m+}\right],$$

$SO_2NR_{24}R_{25}$, S(=O)$R_{24}$, $SO_2R_{24}$ and P(=O)(OR$_{24}$)OR$_{25}$;

$R_{24}$ and $R_{25}$ are each, independently from any other, H, $C_1$-$C_{18}$alkyl, $C_7$-$C_{18}$aralkyl, $C_6$-$C_{24}$aryl or $C_1$-$C_{24}$heteroaryl, or $R_{24}$ and $R_{25}$ are each, independently from any other, H, $C_1$-$C_{18}$alkyl, $C_7$-$C_{18}$aralkyl, $C_6$-$C_{24}$aryl or $C_1$-$C_{24}$heteroaryl and $R_{24}$ and $R_{25}$ are additionally bound together through a direct bond or bridged over a O, S, NH, N—$C_1$-$C_{18}$alkyl, N—$C_7$-$C_{18}$aralkyl, N—$C_6$-$C_{24}$aryl or N—$C_1$-$C_{24}$heteroaryl bridge;

$M^{m+}$ is an organic or inorganic cation;

m is 1, 2, 3 or 4; and n is 1, 2, 3 or 4, wherein the effective, thermally or actinically radicals-generating amount is such that from 0.01 to 30 triazene functional groups N—N=N—$R_7$ are present in the compound (b) of formula (I) per 100 ethylenically unsaturated functional groups C=C of the polymerizable monomer or oligomer (a).

3. A triazene compound of formula (I) as defined in claim 1, wherein the triazene of formula (I) is not of formula

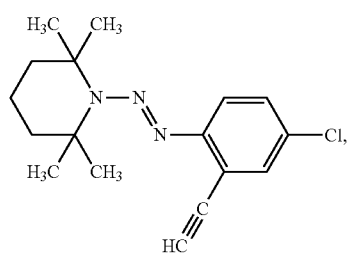

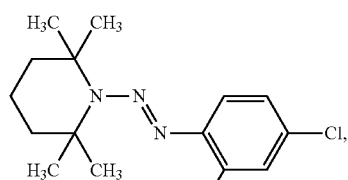

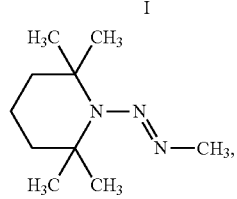

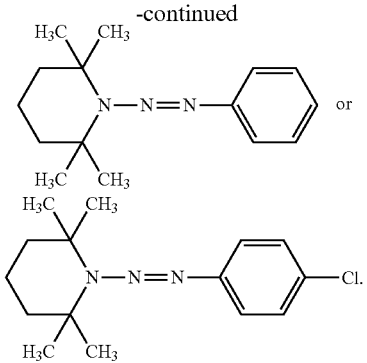

4. The compound of claim 1 of formula:

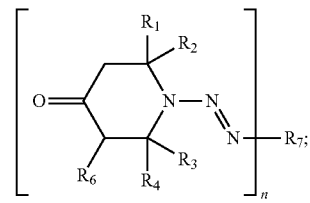
(IIa)

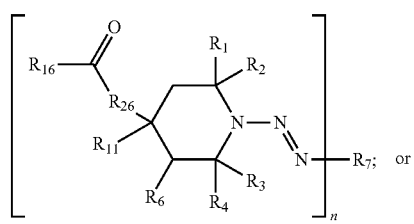
(IIb)

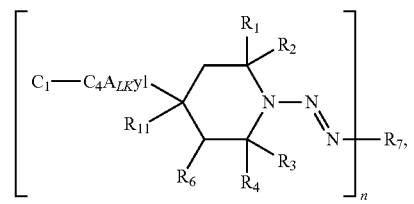
(IIc)

wherein:

$R_1$, $R_2$, $R_3$ and $R_4$ are each, independently from the other, $C_1$-$C_4A_{LK}$yl;

$R_6$ and $R_{11}$ are each, independently from the other, H or $C_1$-$C_4A_{LK}$yl;

$R_7$ is $C_6$-$C_{14}$aryl or $C_1$-$C_{12}$heteroaryl;

$R_{16}$ is H, $R_{18}$, $OR_{18}$, $NR_{18}R_{19}$, $R_{21}$—$COOR_{20}$, $R_{21}$—CON($R_{20}$)$R_{27}$, $R_{22}$(—$COOR_{20}$)—$COOR_{23}$ or $R_{22}$(—CON($R_{20}$)$R_{27}$)—CON($R_{23}$)$R_{28}$;

$R_{18}$ and $R_{19}$ are each, independently from the other, $C_1$-$C_{36}A_{LK}$yl, $C_2$-$C_{54}A_{LK}$enyl, $C_6$-$C_{14}$aryl, $C_7$-$C_{46}$ar$A_{LK}$yl or $C_2$-$C_{36}A_{LK}$enylene-$C_6$-$C_{10}$aryl, or $R_{18}$ and $R_{19}$ are together $C_2$-$C_{36}A_{LK}$ylene or $C_2$-$C_{54}A_{LK}$enylene, which is uninterrupted or once or twice interrupted by —O—, —NH— and/or —N($C_1$-$C_4A_{LK}$yl)- thus forming a ring with the N-atom to which they are attached;

each $R_{20}$ or $R_{23}$ stands for H, $R_{18}$, $OR_{18}$, $NR_{18}R_{19}$, $COOR_{20}$, $R_{21}$—$COOR_{20}$, $R_{22}$(—$COOR_{20}$)—$COOR_{23}$ or

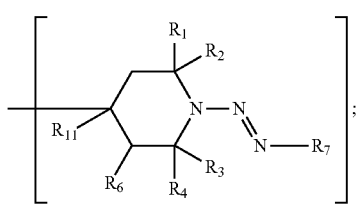

$R_{21}$ is $C_1$-$C_{12}A_{LK}$ylene, $C_2$-$C_{12}A_{LK}$enylene, $C_6$-$C_{10}$arylene or $C_2$-$C_{12}A_{LK}$enylene-$C_6$-$C_{10}$arylene;

$R_{22}$ is $C_1$-$C_{12}A_{LK}$antriyl, $C_2$-$C_{12}A_{LK}$entriyl, benzotriyl, $C_7$-$C_{18}$-benzo$A_{LK}$antriyl, $C_2$-$C_{12}A_{LK}$antriyl-$C_6$-$C_{10}$arylene, $C_2$-$C_{12}A_{LK}$enylene-benzotriyl or $C_2$-$C_{12}A_{LK}$entriyl-$C_6$-$C_{10}$arylene;

$R_{26}$ is O, NH or N($C_1$-$C_4A_{LK}$yl);

$R_{27}$ and $R_{28}$ are each independently from the other H, $C_1$-$C_{24}$alkyl, $C_7$-$C_{24}$aralkyl, $C_6$-$C_{24}$aryl or $C_1$-$C_{24}$heteroaryl;

n is 1 or 2; and $A_{LK}$ is an unsubstituted or substituted hydrocarbon residue as defined in claim 3.

5. The compound of claim 1, wherein $Z_1$ is —($CR_{11}R_{12}$)— and $R_{12}$ is OH, $OR_{14}$, $NH_2$, $NHR_{14}$, $NR_{14}R_{15}$, O—C(=O)—$R_{16}$, NH—C(=O)—$R_{16}$ or $NR_{14}$—C(=O)—$R_{16}$.

6. The compound of claim 1, wherein $R_1$, $R_2$, $R_3$ and $R_4$ are each, independently from the other, $C_1$-$C_6A_{LK}$yl, and $R_5$ and $R_6$ are each, independently from the other, H or $C_1$-$C_6A_{LK}$yl.

7. The compound of claim 1, wherein the total number of C atoms in $R_1$, $R_2$, $R_3$ and $R_4$ is at least 5.

8. A process for the preparation of the compound of claim 3, wherein an amine is coupled with a diazonium salt, a hydrazine is condensed with a nitroso-aromate or a nitroso-heteroaromate, a N-nitrosoamine is condensed with an aminoaromate or an amino-heteroaromate, or a N-alkoxydiazenium salt is condensed with an aminoaromate or an amino-heteroaromate.

9. A method for generating radicals or retarding a flame, the method comprising mixing the compound of claim 3, in a reaction, or applying said compound to a flame.

10. A method for preparing polymeric matter comprising initiating a free-radical polymerization with the composition of claim 1.

11. A process, comprising subjecting the composition of claim 1 to convection heat and/or to UV-, IR- or NIR-radiation.

12. A process for controlled degradation of a polyolefin comprising lowering the molecular weight of said polyolefin with the compound of claim 3, wherein said compound is incorporated into the polyolefin in a concentration of from 0.001 to 5.0% by weight based on the total weight of the polyolefin.

13. The composition of claim 1, wherein $Z_1$ is —($CR_{11}R_{12}$)—.

14. The composition of claim 1, wherein $R_1$ and $R_2$ are together $C_4$-$C_7A_{LK}$ylene thus forming a 5-, 6-, 7- or 8-membered cyclic group with the C-atom to which they are attached.

15. The composition of claim 1, wherein $R_3$ and $R_4$ are together $C_4$-$C_7A_{LK}$ylene thus forming a 5-, 6-, 7- or 8-membered cyclic group with the C-atom to which they are attached.

16. The composition of claim 1, wherein $R_{12}$ is OH, $OR_{14}$, $NH_2$, $NHR_{14}$, $NR_{14}R_{15}$, O—C(=O)—$R_{16}$, NH—C(=O)—$R_{16}$ or $NR_{14}$—C(=O)—$R_{16}$.

17. The composition of claim 1, wherein $R_{11}$ and $R_{12}$ are together $C_2$-$C_{20}A_{LK}$ylene, which is uninterrupted or once or twice interrupted by —O— and/or —$NR_{17}$— thus forming a 5- or 6-membered ring with the C-atom to which they are attached, which $C_2$-$C_{20}A_{LK}$ylene can optionally be annelated with benzo or naphtho, and which $C_2$-$C_{20}A_{LK}$ylene is further unsubstituted or substituted by 1 or 2, identical or different groups —OH or —O—C(=O)—$R_{13}$.

18. The composition of claim 1, wherein $R_{14}$ and $R_{15}$ are together $C_2$-$C_6A_{LK}$ylene, which is uninterrupted or once or twice interrupted by —O— and/or —$NR_{17}$— thus forming a 5- or 6-membered ring with the N-atom to which they are attached.

19. The composition of claim 1, wherein $R_{18}$ and $R_{19}$ are together $C_2$-$C_{36}A_{LK}$ylene or $C_2$-$C_{54}A_{LK}$enylene, which is uninterrupted or once or twice interrupted by —O— and/or —$NR_{17}$— thus forming a 5- or 6-membered ring with the N-atom to which they are attached.

20. The composition of claim 1, wherein n is 1 or 2.

\* \* \* \* \*